(12) United States Patent
Besse

(10) Patent No.: US 7,163,699 B2
(45) Date of Patent: Jan. 16, 2007

(54) PROGESTIN CO-MICRONIZED WITH A SURFACTANT PHARMACEUTICAL COMPOSITION COMPRISING SAME METHODS FOR MAKING SAME AND USES THEREOF

(75) Inventor: Jerome Besse, Listrac Medoc (FR)

(73) Assignee: Laboratories Besins International, Paris (FR)

( * ) Notice: Subject to any disclaimer, the term of this patent is extended or adjusted under 35 U.S.C. 154(b) by 284 days.

(21) Appl. No.: 10/469,441

(22) PCT Filed: Feb. 27, 2002

(86) PCT No.: PCT/FR02/00714

§ 371 (c)(1),
(2), (4) Date: Feb. 10, 2004

(87) PCT Pub. No.: WO02/069978

PCT Pub. Date: Sep. 12, 2002

(65) Prior Publication Data

US 2004/0131553 A1    Jul. 8, 2004

(30) Foreign Application Priority Data

Mar. 1, 2001 (FR) .................................. 01 02814

(51) Int. Cl.
*A61K 9/14* (2006.01)
*A61K 9/16* (2006.01)
*A61K 9/20* (2006.01)
*A61K 9/48* (2006.01)

(52) U.S. Cl. ..................... 424/489; 424/465; 424/456; 424/484

(58) Field of Classification Search ................ 424/489, 424/465, 484, 456
See application file for complete search history.

(56) References Cited

U.S. PATENT DOCUMENTS

| | | | |
|---|---|---|---|
| 4,196,188 | A | 4/1980 | Besins |
| 4,895,726 | A | 1/1990 | Curtet et al. |
| 6,063,404 | A | 5/2000 | Timpe et al. |
| 6,086,916 | A | 7/2000 | Agnus et al. |
| 6,124,358 | A | 9/2000 | Estanove et al. |

FOREIGN PATENT DOCUMENTS

| | | |
|---|---|---|
| FR | 2 775 599 | 3/1998 |
| WO | WO 89/02742 | 10/1988 |
| WO | WO 00/28970 | 11/1999 |

*Primary Examiner*—Edward J. Webman
(74) *Attorney, Agent, or Firm*—Foley & Lardner LLP

(57) ABSTRACT

The invention concerns a progestin co-micronized with a surfactant and a pharmaceutical composition comprising said gestagenic. The invention also concerns methods for preparing same.

36 Claims, 2 Drawing Sheets

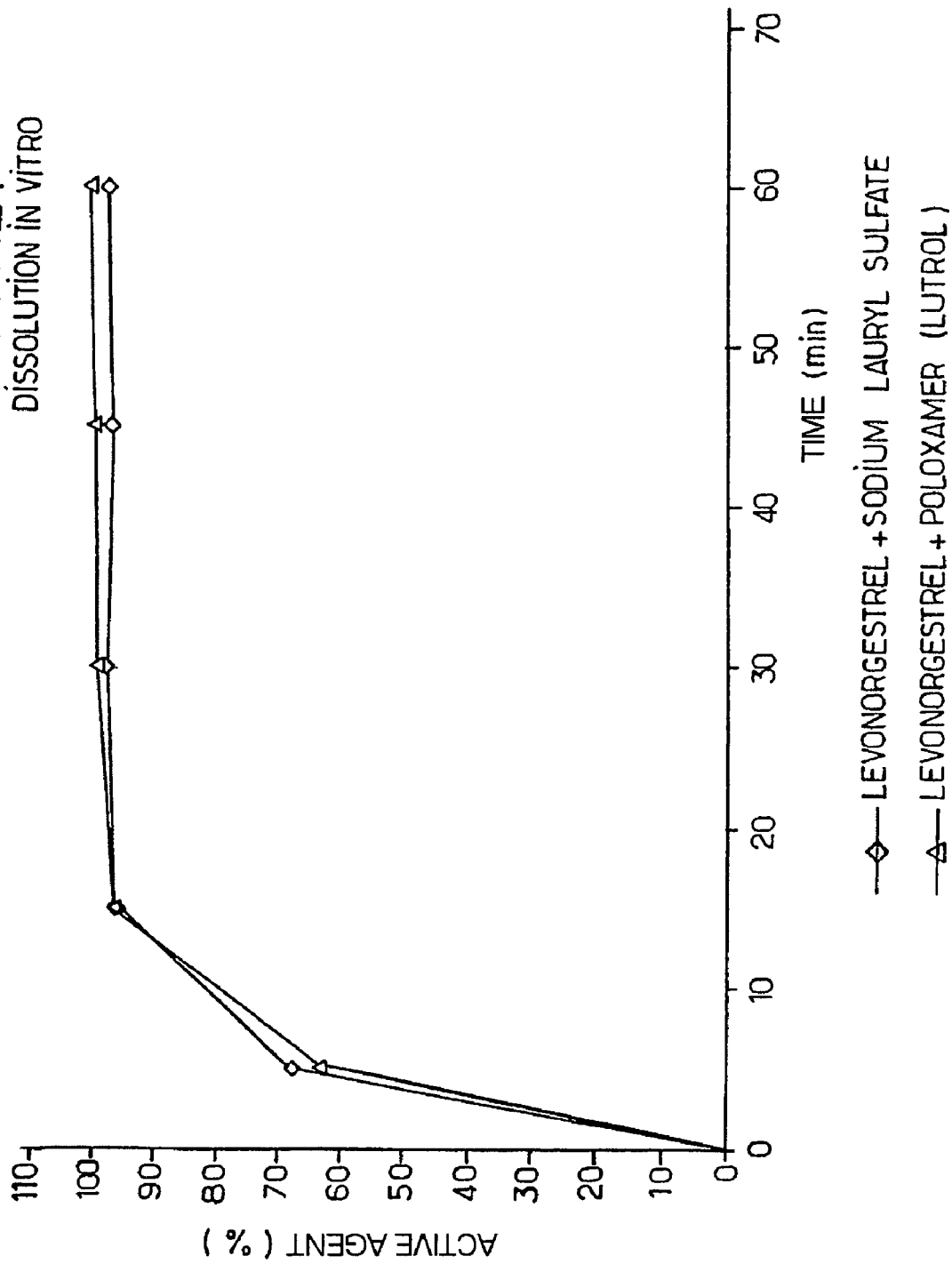

PROGESTIN CO-MICRONIZED WITH A SURFACTANT PHARMACEUTICAL COMPOSITION COMPRISING SAME METHODS FOR MAKING SAME AND USES THEREOF

The present invention relates, as a new product, to a progestin co-micronized with a surfactant, to a pharmaceutical composition containing same, to methods for preparing same, and also to uses thereof.

In the context of the present invention, the term "progestin" is intended to mean any steroid having affinities for progesterone receptors and capable of more or less fully reproducing the biological effects of progesterone.

A progestin is a compound capable, by definition, of maintaining gestation and of promoting implantation of the egg. This biological role is reflected essentially by a change in the vaginal mucosa (desquamation), in the endometrium (cell proliferation, formation of the uterine lining), and in the endocervical glandular epithelium (decrease in the production of glairy mucus and thickening thereof).

The only property that all progestins have in common is their endometrial action.

The effect on gestation is real for progesterone and very inconstant with synthetic progestins.

Progestins comprise progesterone and also synthetic progestins. The latter may be classified into three groups (unofficial classification) according to their biological activities (and their structure, which determines said activities); the order of classification thus takes into account their structural difference relative to physiological progesterone.

The first group comprises molecules similar to progesterone or synthetic progestins 1 (SP1) (pregnanes), for example the progesterone isomer (retroprogesterone), Medrogesterone, norprogesterone derivatives (demegestone or promegestone). These molecules have peripheral extragestative activity which is virtually identical to progesterone, and have no androgenic effects.

The second group comprises 17α-hydroxyprogesterone derivatives or synthetic progestins 2 (SP2) (pregnanes), for example cyproterone acetate and medroxyprogesterone acetate. These molecules have more powerful and more intense peripheral gestative activity than that of progesterone and, in addition, have an androgenic effect.

The third group comprises the norsteroids or synthetic progestins 3 (SP3) (estranes or norandrostanes). These are 19-nortestosterone derivatives, for example norethindrone. These molecules have particularly powerful peripheral gestative activity (this is the group of synthetic progestins which has the most pronounced endometrial action) and also have an androgenic effect. From these norandrostanes or estranes are derived molecules of the gonane type containing a methyl group at C18 and an ethyl group at C13. Examples that may be mentioned include norgestimate (levonorgestrel), desogestrel (3-keto desogestrel) and gestodene. These chemical modifications increase the endometrial power and decrease the intrinsic androgenic activity of the molecule.

Progesterone is a hormone which is synthesized, in women, essentially by the ovary during the post-ovulatory or luteal (yellow body) phase and, to a lesser degree, by the adrenal glands and the placenta during the second part of pregnancy. A non-endocrine synthesis of progesterone, in particular in the neurones, is also possible.

The consequence of insufficiency of progesterone secretion in women is a loss of its biological effects: progestin effect; anti-androgenic effect (action on the skin) and anti-estrogenic effect (a consequence of which is hyperestrogenism: hot flushes, psychogenic difficulties such as anxiety or depression, weight gain, etc.). This progesterone insufficiency may lead to functional impairment and various clinical manifestations, in particular:
  premenstrual syndromes,
  menstrual irregularities through disovulation or anovulation,
  benign mastopathies,
  perimenopause and menopause.

The use of hormone replacement therapy is well established to date for relieving menopausal symptoms. Given that it has been demonstrated that progestins prevent the development of hyperplasia and endometrial cancer, sequential or combined therapy with estrogens and progestins is advised in menopausal women who have not undergone a hysterectomy. Among progestins suitable for hormone replacement therapy, micronized progesterone is preferably used due to its lack of androgenic effect and its metabolic innocuity.

However, oral administration of progesterone suffers from a serious handicap due to the considerable metabolizing thereof in the liver.

Now, the oral administration method has clear advantages compared to other methods of its administration. Specifically, it is, firstly, more practical than vaginal administration and, secondly, it allows a dose to be taken independently, which is impossible with parenteral administration.

LABORATORIES BESINS-ISCOVESCO have already proposed a solution to this problem of progesterone degradation, in patent application FR 76 36007. Specifically, they have developed a formulation of soft capsules containing progesterone micronized in oily suspension, which allows improved bioavailability of the progesterone.

The method for preparing such capsules proves, however, to be complex and expensive to carry out, and also requires considerable know-how. Attempts have therefore been made to develop alternative effective, but also economically viable, formulations such as progesterone-based tablets (see patent applications FR 97 16168 and FR 98 02830).

However, there is still a need to find pharmaceutical formulations containing progesterone or another progestin and having improved bioavailability.

In general, the bioavailability of an active principle can be improved by chemical means: administration of prodrugs, complexation, combination with lipids or phospholipids, most often in the presence of a surfactant; or by physical means such as micronization.

Micronization is a well-known technique which can be carried out either in hammer or ball mills or in gas jet micronizers. As was recalled above, the micronization technique has already been used (see BESINS patent FR 76 36007) to develop a composition based on progesterone which is bioavailable and which can be administered orally.

Patent application FR 2 757 397 also recalls this fact and subsequently indicates, on page 2, that co-micronization of phenofibrate in the presence of sodium lauryl sulfate has already been described in patent EP 330 532. However, that patent application underlines, at the same time, the fact that it is not automatic and inescapable that the bioavailability of an active principle is systematically improved by co-micronization in the presence of a surfactant. Thus, the inventors of that patent application recall that M. OTSUDA et al. (JPS 84, 1995, p. 1434–37) studied the micronization of phenitoin in the presence of a surfactant and that they showed that the solubility of phenitoin is not improved in the case of co-micronization with a surfactant such as sodium lauryl sulfate or a sucrose ester of stearic acid, whereas it is multiplied by 30 compared to the mixture of powders in the case of co-grinding with sodium deoxycholate.

The same authors underlined moreover—which is entirely relevant—that even though micronization or grinding of a substance in the presence of a surfactant or of a sugar can increase its solubility, these parameters are not always sufficient. They thus gave, as an example, the fact that the bioavailability of micronized progesterone is not satisfactory and that it must be improved, for example by mixing the micronized progesterone with carnauba wax, a technique described in patent application WO 89/02742.

It is therefore perfectly established that the properties of a substance treated by micronization or grinding, in particular its solubility and its bioavailability, are not predictable, contradictory results possibly being obtained, and that the same pharmaceutical formulation can provide good results with one substance and produce an opposite result with another substance.

Now, it is to the applicant company's credit to have succeeded in improving not only the solubility but also the bioavailability of progestins, including most particularly progesterone, by carrying out their co-micronization in the presence of a surfactant, which was neither taught nor even suggested by the documents of the prior art.

A subject of the invention is therefore, as a novel product, a progestin co-micronized with a surfactant, and also a pharmaceutical composition containing said co-micronized progestin. Subjects of the invention are also the method for producing the co-micronized progestin, the method for producing the pharmaceutical composition comprising the co-micronized progestin, and also the use of said progestin for preparing a medicinal product intended to prevent or treat disorders or diseases caused by a progestin insufficiency.

For the purpose of the present invention, the term "surfactant" is intended to mean any product having both a lipophilic component and a hydrophilic component. These products are generally classified as ionic or nonionic. In accordance with the present invention, an ionic surfactant is preferably used. Even more preferentially, sodium lauryl sulfate is used.

Co-micronization of progesterone or of another progestin with a surfactant, in particular sodium lauryl sulfate, makes it possible to improve the solubility of the active principle, allowing rapid in vitro dissolution profiles to be obtained. Co-micronization also makes it possible to improve the wettability of the progestin when it is administered per os thus facilitating its absorption in vivo.

According to an advantageous embodiment of the invention, the co-micronized progestin is progesterone and the surfactant is sodium lauryl sulfate.

The surfactant content is at least equal to the critical micellar concentration of the progestin/surfactant combination.

The co-micronized progestin in accordance with the invention exhibits a progestin content of between 80.0% and 99.9%, preferably between 90.0% and 99.5%, and even more preferentially between 95.0% and 99.0%, and a surfactant content of between 0.1% and 20%, preferably between 0.5% and 10.0%, and even more preferentially between 1.0% and 5.0%, the percentages being expressed by weight of solids.

When the progestin is progesterone, the surfactant/progesterone ratio is between 1/200 and 1/20, preferably between 1/150 and 1/40.

A subject of the invention is also a pharmaceutical composition comprising the progestin co-micronized with a surfactant as described above.

According to an advantageous embodiment, the pharmaceutical composition in accordance with the invention exhibits a surfactant content of between 0.001% and 5%, preferably between 0.002% and 3%, and even more preferentially between 0.005% and 2%, relative to the total solids.

When the co-micronized progestin is progesterone, the surfactant content is then between 0.1% and 5%, preferably between 0.2% and 3%, even more preferentially between 0.2% and 2%, by weight relative to the total solids of the pharmaceutical composition.

The pharmaceutical composition according to the present invention can be in the form, for example, of a soft capsule, of a gelatin capsule, of a tablet, of a lyophilisate, of a powder or of a granule, including microgranules. Preferably, the pharmaceutical composition according to the invention is a tablet.

When it is a tablet, the pharmaceutical composition according to the invention contains excipients for in particular facilitating compression in order to obtain a tablet having good hardness, disaggregation and dissolution characteristics.

As excipients which can be used in the tablet according to the invention, mention may be made of diluents, disintegrating agents, lubricants, binders and dyes conventionally used in this application.

As examples of diluents, mention may be made of sugars, starches, polyols and celluloses, and derivatives. Preferably, the tablet according to the invention contains lactose and/or mannitol as diluents.

As examples of disintegrating agents, mention may be made of carboxymethylcelluloses, alginic acid and also its sodium salt, and modified starches. Preferably, the tablet according to the invention contains crosslinked sodium carboxymethylcellulose (also referred to as sodium croscarmellose).

The preferred lubricant used in the context of the present invention is magnesium stearate.

Among the preferred binders in the context of the production of the tablet according to the present invention, mention may be made of polyvinyl-pyrrolidones. Preferably, the tablet according to the invention contains polyvidone K30.

The tablet according to the invention may also contain a dye, such as, for example, the dye orange yellow S or Pigment Blend PB 23028.

The pharmaceutical composition according to the invention may also contain an estrogen or one of its derivatives.

In fact, estrogens, particularly 17β-estradiol, are prescribed in order to reduce the harmful consequences associated with their disappearance during menopause, such as osteoporosis, hot flushes or cardiovascular accidents. The long-term administration of estrogens alone presents major risks given in particular the possible carcinogenic role of this hormone. It is usual to combine with it a treatment with a progestin in order to avoid the risks of endometrial hyperplasia.

The estrogen which may be included in the pharmaceutical composition according to the present invention can be selected from the estrogens which are active per os, i.e. natural estrogens (17β-estradiol, estrone) or synthetic estrogens (17α-ethinylestradiol or estradiol valerate). 17β-estradiol is preferably used.

The estrogen content of the pharmaceutical composition according to the invention is between 0.05% and 5%, preferably between 0.1% and 3%.

A subject of the invention is also a method for co-micronization of a progestin with a surfactant. This co-micronized material can be produced from a solid/solid mixture (as in the case of the progesterone/sodium lauryl sulfate mixture) using an airjet mill, such as the one marketed under the trade mark ALPINE.

In the case of a solid/liquid co-micronized material (example: progesterone/TWEEN 80), the co-micronization operation can be carried out with a colloidal mill or else a ball mill.

The method for preparing the progestin co-micronized with a surfactant is therefore characterized in that a mixture of a progestin with a surfactant is prepared, and in that either a grinding step is then carried out with an air jet mill, in the case of a solid/solid co-micronization, or a grinding step is then carried out with a colloidal mill or a ball mill, in the case of a solid/liquid co-micronization.

When the pharmaceutical composition according to the invention is in the form of a tablet, the method for preparing a progestin-based tablet preferentially comprises the following steps:

preparing a first mixture of progestin and surfactant,
micronizing this first mixture in order to obtain a progestin co-micronized with the surfactant,
preparing a wetting solution,
wetting the progestin co-micronized with the surfactant, with the wetting solution,
granulating the mixture obtained in order to obtain granules,
drying the granules and then calibrating,
adding to the calibrated granules disintegrating agents, diluents, dyes, lubricants,
compressing the mixture thus obtained in order to obtain tablets.

The invention also relates to the use of a progestin co-micronized with a surfactant as defined above, for preparing a medicinal product intended for the treatment of a physiological condition related to insufficiency of progesterone secretion, such as menopause.

BRIEF DESCRIPTION OF THE DRAWINGS

FIG. 2. Dissolution of levonorgestrel.

Figure 1:
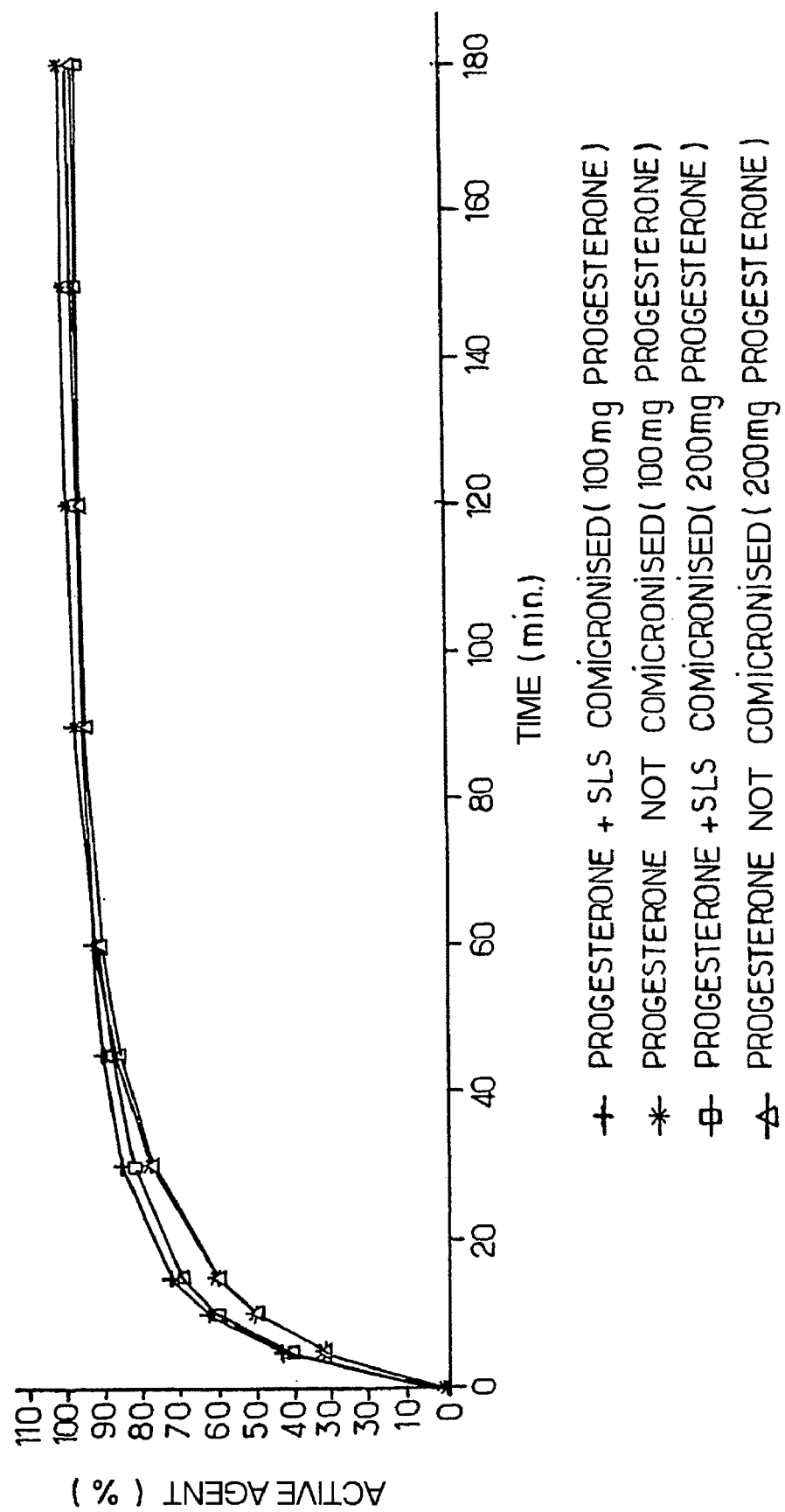
FIG. 1. Dissolution of progesterone.

The invention will be understood more clearly from the nonlimiting examples described below.

EXAMPLE 1

Preparation of Progesterone Co-Micronized with Sodium Lauryl Sulfate 1) 97 g of progesterone and 3 g of sodium lauryl sulfate are mixed for 5 minutes in a mixer of the LÖDIGE type.
2) The mixture obtained in step (1) is introduced into an Alpine 200 AS airjet mill preset on the following parameters:

| | | |
|---|---|---|
| injection: | 5.5 B | |
| ring: | 3.0 B | |
| rate: | 35 kg/h | |

3) This mixture is ground in order to obtain a co-micronized material of progesterone/sodium lauryl sulfate.

EXAMPLE 2

Tablets Based on Progesterone Co-Micronized with a Surfactant

The formulations of progesterone tablets according to the invention, containing 100 and 200 mg of progesterone, are given in Table I below.

TABLE 1

| NAME OF THE COMPONENT | FUNCTION | UNIT AMOUNT mg/tablet | | BATCH SIZE (kg) |
|---|---|---|---|---|
| Micronized progesterone* | Active principle (progestin) | 200 | 100 | 55.000 |
| (sodium lauryl sulfate (SLS))* | (surfactant) | 6.18 | 3.09 | |
| Povidone K30 Solution at 35% (m/m) | Binder | 9.60 | 4.80 | 2.561 |
| Mannitol | Diluent | 29.84 | 14.92 | 7.981 |
| Crosslinked sodium carboxymethylcellulose | Disintegrating agent | 13.00 | 6.50 | 3.468 |
| Magnesium stearate | Lubricant | 1.30 | 0.65 | 0.347 |

*Progesterone/SLS are co-micronized according to example 1.

To prepare the tablets in question, the following procedure was carried out:

Step 1: Preparation of the Wetting Solution 4.756 kg of purified water are introduced into a container of suitable volume. 2.561 kg of Povidone K30 are then introduced into the purified water, gradually, and with stirring in a deflocculating-type stirrer (RAYNERI) at a stirring rate of approximately 1800 rpm and for 30 minutes until complete solubilization of the Povidone K30.

Step 2: Granulation 55.000 kg of co-micronized progesterone are introduced into the tank of a LÖDIGE-type mixer.

The preceding mixture is wetted with the solutions from step 2, and granulation is then carried out until a satisfactory visual appearance is obtained.

The conditions for the granulation are as follows:

| Amount of purified water added as QS Satisfactory final appearance of the grain | |
|---|---|
| % residual water content | 6.8 |
| Duration of wetting (approximately 1 min) | 30 sec |
| Duration of granulation (plowshare + blade) | 5 min 30 sec |
| Power absorbed (fine granulates) | (approximately 38%). |

Wet decaking of the grain on leaving the granulator can be carried out if necessary before drying on an ALEXANDER-WERK rotary calibrator or equivalent equipped with a stainless steel screen greater than or equal to 3 mm in diameter.

Step 3: Drying

The grain from step 2 is dried until a satisfactory residual water content is obtained.

The drying conditions are as follows:
inlet air temperature (approximately 55° C.)
outlet air temperature: 39° C. end at 42° C. (at the end of drying)
duration: 10 min.

Step 4: Calibration

The grain from step 3 is calibrated on a BOHLE equipped with a screen of mesh size 1.0 mm, or equivalent.

The calibration conditions are as follows:
duration: 12 min
amount obtained: 55.040 kg
% residual water content of the calibrated grain.

Homogenization is carried out for 5 min at 5 rpm in a BOHLE or equivalent.

Step 5: Mixing

The following are introduced into the MCG 600 tank of the BOHLE PM 100 mixer of suitable capacity, or equivalent:
the calibrated grain from step 4: 54.740 kg
croscarmellose: 3.298 kg
mannitol: 7.590 kg Mixing is carried out at a speed of 5 rpm for approximately 30 min.

Step 6: Lubrication 0.330 kg of magnesium stearate are introduced into the mixture from step 5:

Mixing is carried out at a speed of 5 rpm for approximately 10 min.

The net weight is 64.490 kg.

The mixture is stored in an air-tight container.

Step 7: Compression

The compressing machine of the KILIAN RTS 21 type, or equivalent, is equipped with punches of 7R7.5-type format for progesterone 100 mg and 9R10-type format for progesterone 200 mg.

The hopper of the compressing machine is fed with the mixture from step 6.

The compression settings are adjusted so as to obtain tablets with a mass of 130 mg, and with a satisfactory hardness and thickness making it possible to guarantee a disintegration time of less than 5 min.

EXAMPLE 3

Dissolving of the Progesterone Tablets Prepared According to the Invention, In Vitro 100 mg and 200 mg progesterone tablets are prepared according to the method given in example 2, and the following operations are carried out in order to determine the in vitro dissolution curves (see FIG. 1).

The following material is used:
SOTAX AT7 7-position revolving-paddle dissolution device
PERKIN ELMER lambda 20 spectrophotometer
ISMATEC IPC 12 cassette pump
WINSOTAX data acquisition software.

The dissolving conditions are as follows:
dissolving medium: 1000 ml of aqueous solution of β-hydroxypropylcyclodextrin having the trade mark KLEPTOSE® at 1% per cell
rotation rate: 150 rpm
temperature: 37° C.±0.5° C.
number of cells: 7 circulation cell made of quartz with an optical path: 0.1 cm.

A control is prepared, consisting of a tablet of micronized progesterone:

| | |
|---|---|
| Progesterone | 20 mg |
| HPLC ethanol | 2 ml |
| 1% solution of KLEPTOSE ® | qs 200 ml |

The agitation is carried out using rotating buckets.

Procedure

1—The cells are placed in the waterbath at ambient temperature.

2—1000 ml of 1% KLEPTOSE® solution are transferred into each one of the 7 cells.

3—One tablet is placed in 6 of the 7 rotating buckets. Cell 7 is used as an in-test reference.

4—The rotating buckets are immersed in the dissolving medium at a distance of 25 mm±2 mm between the rotating bucket and the bottom of the cell.

5—The buckets are agitated at 150 rpm.

6—At each planned time interval, the amount of medium necessary and sufficient to determine the concentration of dissolved active principle is automatically sampled from each one of the 7 cells. This measurement is carried out with the device described above.

7—Each sample collected is assayed by spectrophotometry ($\lambda$=248 nm).

8—The percentage of released progesterone is determined. The results are given in table II below and also in FIG. 1.

Legend:

GAL 207.07: 100 mg progesterone tablet batch 102 (progesterone/sodium lauryl sulfate co-micronization).

GAL 208.03: 200 mg progesterone tablet batch 101 (progesterone/sodium lauryl sulfate co-micronization).

GAL 208.04: 100 mg progesterone tablet active principle not co-micronized batch 00VR1108.01.

TABLE II

| | % of dissolved progesterone (mean of 6 cells) | | | |
|---|---|---|---|---|
| Time (in min) | GAL 207.07 batch 102 | GAL 207.08 batch 00VR1108.01 | GAL 208.03 batch 101 | GAL 208.04 batch 00VR1110.01 |
| 0 | 0 | 0 | 0 | 0 |
| 5 | 42.97 | 32.35 | 40.31 | 32.06 |
| 10 | 62.43 | 50.29 | 60.37 | 49.42 |
| 15 | 72.26 | 60.64 | 69.74 | 59.90 |
| 30 | 85.59 | 78.21 | 82.35 | 77.21 |
| 45 | 90.79 | 87.45 | 88.21 | 86.18 |
| 60 | 93.38 | 92.81 | 91.48 | 90.99 |
| 90 | 95.95 | 98.09 | 94.85 | 95.61 |
| 120 | 97.32 | 100.26 | 96.49 | 97.71 |
| 150 | 98.02 | 101.26 | 97.45 | 98.88 |
| 180 | 98.46 | 101.81 | 97.31 | 99.56 |

EXAMPLE 4

Tablets According to the Invention Containing a Progestin Co-Micronized with a Surfactant The formulations of tablets according to the invention containing either progesterone or levonogestrel are given tables III to V below.

TABLE III

| NAME OF THE COMPONENT | FUNCTION | UNIT AMOUNT mg/tablet | % TABLET |
|---|---|---|---|
| Micronized progesterone* | Progestin active principle | 100 | 77.00 |
| LUTROL ® F127* (poloxamer 407) | Surfactant (poloxamer) | 3.09 | 2.30 |
| Kollidonr ® 30 (Povidone K30) | Binder | 8.31 | 6.39 |
| Pearlitol ® 500DC (Mannitol) | Diluent | 11.45 | 8.81 |
| AcDiSol ® (Crosscarmellose) | Disintegrating agent | 6.50 | 5.00 |
| Magnesium stearate | Lubricant | 0.65 | 0.50 |

*Progesterone/Lutrol are co-micronized according to the protocol mentioned in example 1.

TABLE IV

| NAME OF THE COMPONENT | FUNCTION | UNIT AMOUNT mg/tablet | % TABLET |
|---|---|---|---|
| Levonorgestrel* | Progestin active principle | 0.75 | 0.58 |
| Sodium lauryl sulfate (SLS) | Surfactant | 0.023 | 0.02 |
| Mannitol 60 | Diluent | 102.303 | 78.69 |
| Kollidon ® 30 (Povidone K30) | Binder | 4.194 | 3.23 |
| Pearlitol ® 500DC (mannitol) | Diluent | 15.58 | 11.98 |
| AcDiSol ® (Crosscarmellose) | Disintegrating agent | 6.50 | 5.00 |
| Magnesium stearate | Lubricant | 0.65 | 0.50 |

*Levonorgestrel/SLS are co-micronized according to the protocol mentioned in example 1.

TABLE V

| NAME OF THE COMPONENT | FUNCTION | UNIT AMOUNT mg/tablet | % TABLET |
|---|---|---|---|
| Levonorgestrel* | Progestin active principle | 0.75 | 0.58 |
| Lutrol ® F127 (poloxamer 407) | Surfactant | 0.023 | 0.02 |
| Mannitol 60 | Diluent | 102.3 | 78.69 |
| Kollidon ® 30 (Povidone K30) | Binder | 4.194 | 3.23 |
| Pearlitol ® 500DC (mannitol) | Diluent | 15.58 | 11.98 |
| AcDiSol ® (Crosscarmellose) | Disintegrating agent | 6.50 | 5.00 |
| Magnesium stearate | Lubricant | 0.65 | 0.50 |

*Levonorgestrel/Lutrol are co-micronized according to the protocol mentioned in example 1.

FIG. 2 shows in vitro dissolution tests for the formulations given in tables IV and V.

These curves demonstrate that the active principle co-micronized is released in a very satisfactory manner.

The invention claimed is:

1. A progestin co-micronized with a surfactant comprising a progestin content of between 80.0% and 99.9%, and a surfactant content of between 0.1% and 20.0%, the percentages being expressed by weight of solids.

2. The co-micronized progestin as claimed in claim 1, wherein the progestin is progesterone.

3. The co-micronized progestin as claimed in claim 1, wherein the surfactant is sodium lauryl sulfate.

4. The co-micronized progestin as claimed in claim 1, comprising a progestin content of between 90.0% and 99.5%, and a surfactant content of between 0.5% and 10.0%, the percentages being expressed by weight of solids.

5. A progesterone co-micronized with a surfactant as claimed in claim 2, wherein the surfactant/progesterone ratio is between 1/200 and 1/20.

6. A pharmaceutical composition comprising the progestin co-micronized with a surfactant as claimed in claim 1.

7. A pharmaceutical composition comprising the progesterone co-micronized with a surfactant as claimed in claim 2.

8. The pharmaceutical composition as claimed in claims 6, comprising a surfactant content of between 0.001% and 5%, relative to the total solids of the composition.

9. The pharmaceutical composition as claimed in claim 8, comprising a surfactant content of between 0.1% and 5%, by weight relative to the total solids of the composition.

10. The pharmaceutical composition as claimed in claim 6, in a form selected from the group constituted by a soft capsule, a gelatin capsule, a tablet, or a lyophilisate, or a powder or a granule, including microgranules.

11. The pharmaceutical composition as claimed in claim 6, comprising, in addition to the co-micronized progestin, an estrogen or one of its derivatives.

12. The pharmaceutical composition as claimed in claim 11, wherein the estrogen is selected from the group consisting of 17 β-estradiol, estrone, 17 α-ethinylestradiol and estradiol valerate.

13. The pharmaceutical composition as claimed in claim 12, comprising an estrogen content of between 0.05% and 5%.

14. A method for co-micronization of a progestin with a surfactant, wherein a mixture of a progestin with a surfactant is prepared, and then grinding of this mixture is subsequently carried out using an airjet mill, a colloidal mill or a ball mill.

15. A method for preparing a tablet based on a progestin, preferably progesterone, wherein:
   a first mixture of progestin and surfactant is prepared,
   this first mixture is micronized in order to obtain a progestin co-micronized with the surfactant,
   a wetting solution is prepared,
   the progestin co-micronized with the surfactant is wetted with the wetting solution,
   the mixture obtained is granulated in order to obtain granules,
   the granules are dried and are then calibrated,
   disintegrating agents, diluents, dyes, lubricants are added to the dried and calibrated granules,
   this mixture is compressed in order to obtain tablets.

16. The method of preparation as claimed in claim 15, wherein the surfactant is sodium lauryl sulfate.

17. A medicinal product for the treatment of a physiological condition related to insufficiency of progesterone secretion, such as menopause comprising a progestin co-micronized with a surfactant as claimed in claim 1.

18. The co-micronized progestin as claimed claim 4, comprising a progestin content of between 95.0% and 99.0%, and a surfactant content of between 1.0% and 5.0%, the percentages being expressed by weight of solids.

19. The progesterone co-micronized with a surfactant as claimed in claim 5, wherein the surfactant is sodium lauryl sulfate.

20. The progesterone co-micronized with a surfactant as claimed in claim 5, wherein the surfactant/progesterone ratio is between 1/150 and 1/40.

21. The progesterone co-micronized with a surfactant as claimed in claimed 20, wherein the surfactant is sodium lauryl sulfate.

22. The pharmaceutical composition as claimed in claim 8, comprising a surfactant content of between 0.002% and 3%, relative to the total solids of the composition.

23. The pharmaceutical composition as claimed in claim 22, comprising a surfactant content of between 0.005% and 2%, relative to the total solids of the composition.

24. The pharmaceutical composition as claimed in claim 23, comprising a surfactant content of between 0.2% and 3%, by weight relative to the total solids of the composition.

25. The pharmaceutical composition as claimed in claim 24, comprising a surfactant content of between 0.2% and 2%, by weight relative to the total solids of the composition.

26. The pharmaceutical composition as claimed in claim 7, comprising a surfactant content of between 0.001% and 5%, relative to the total solids of the composition.

27. The pharmaceutical composition as claimed in claim 26, comprising a surfactant content of between 0.002% and 3%, relative to the total solids of the composition.

28. The pharmaceutical composition as claimed in claim 27, comprising a surfactant content of between 0.005% and 2%, relative to the total solids of the composition.

29. The pharmaceutical composition as claimed in claim 28, comprising a surfactant content of between 0.1% and 5%, by weight relative to the total solids of the composition.

30. The pharmaceutical composition as claimed in claim 28, comprising a surfactant content of between 0.2% and 3%, by weight relative to the total solids of the composition.

31. The pharmaceutical composition as claimed in claim 30, comprising a surfactant content of between 0.2% and 2%, by weight relative to the total solids of the composition.

32. The pharmaceutical composition as claimed in claim 7, being in the form of a soft capsule, of a gelatin capsule, of a tablet, or of a lyophilisate, or of a powder or of a granule, including microgranules.

33. The pharmaceutical composition as claimed in claim 7, comprising, in addition to the co-micronized progesterone, an estrogen or one of its derivatives.

34. The pharmaceutical composition as claimed in claim 33, wherein the estrogen is selected from the group consisting of 17 β-estradiol, estrone, 17 α-ethinylestradiol and estradiol valerate.

35. The pharmaceutical composition as claimed in claim 34, comprising an estrogen content of between 0.05% and 5%.

36. The pharmaceutical composition as claimed in claim 35, comprising an estrogen content of between 0.1% and 3%.

* * * * *